United States Patent
Ziegler

(10) Patent No.: US 12,365,925 B2
(45) Date of Patent: Jul. 22, 2025

(54) METHOD AND SYSTEM FOR TREATMENT OF MICROORGANISMS DURING PROPAGATION, CONDITIONING, FERMENTATION, AND PRESERVATION USING ETHYL LAUROYL ARGINATE AND SELECTED ADDITIVES

(71) Applicant: KEMIN INDUSTRIES, INC., Des Moines, IA (US)

(72) Inventor: Allen M. Ziegler, Littleton, CO (US)

(73) Assignee: KEMIN INDUSTRIES, INC., Des Moines, IA (US)

(*) Notice: Subject to any disclaimer, the term of this patent is extended or adjusted under 35 U.S.C. 154(b) by 0 days.

(21) Appl. No.: 15/558,700

(22) PCT Filed: Jul. 5, 2016

(86) PCT No.: PCT/US2016/041015
§ 371 (c)(1),
(2) Date: Sep. 15, 2017

(87) PCT Pub. No.: WO2017/007776
PCT Pub. Date: Jan. 12, 2017

(65) Prior Publication Data
US 2018/0112238 A1    Apr. 26, 2018

Related U.S. Application Data

(60) Provisional application No. 62/197,994, filed on Jul. 28, 2015, provisional application No. 62/189,146, filed on Jul. 6, 2015.

(51) Int. Cl.
*C12P 7/10*    (2006.01)
*A01N 47/44*    (2006.01)
(Continued)

(52) U.S. Cl.
CPC ............... *C12P 7/10* (2013.01); *A01N 47/44* (2013.01); *A23B 2/729* (2025.01); *A23B 2/742* (2025.01);
(Continued)

(58) Field of Classification Search
None
See application file for complete search history.

(56) References Cited

U.S. PATENT DOCUMENTS 8,772,002 B1 *   7/2014   Chapman .................. C12P 7/06
                                                         435/165
2007/0264401 A1   11/2007   Taormina et al.
(Continued)

FOREIGN PATENT DOCUMENTS

EP    1998615 B1    8/2010

OTHER PUBLICATIONS

International Search Report for PCT/US2016/041015, dated Oct. 21, 2016 (four pages).
(Continued)

*Primary Examiner* — Erin M. Bowers
(74) *Attorney, Agent, or Firm* — NYEMASTER GOODE P.C.

(57) ABSTRACT

What is disclosed is a method of reducing undesirable concentrations of microorganisms without the use of man-made antibiotics, comprising the steps of: introducing a quantity of fermentable carbohydrate; sugar or cellulose to an aqueous system; introducing a quantity of desirable microorganism to the aqueous system; introducing at least one acid into the aqueous system, wherein the at least one acid is selected from the group consisting of hops acid, organic acid, or a combination of hops acid and organic acid; and introducing a compound comprised of Lauryl-L-arginine ethyl ester monohydrochloride (LAE) into the aqueous
(Continued)

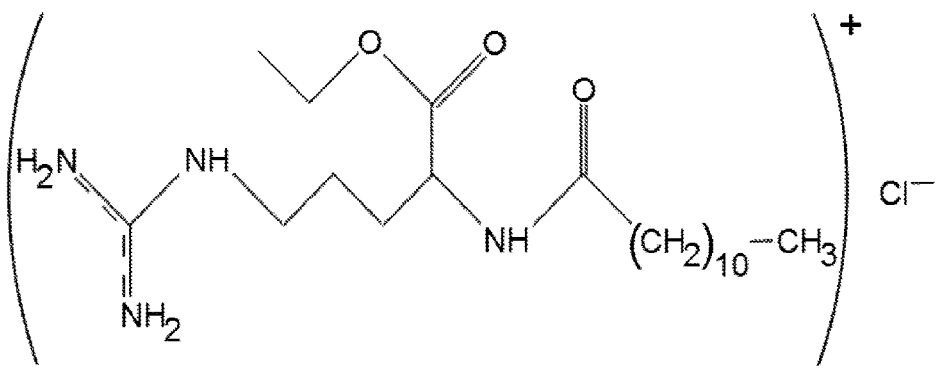

Formula: $C_{33}H_{47}NO_{13}$

Structure:

system. The use of LAE as a preservative of distiller's grains and solubles is also disclosed.

18 Claims, 5 Drawing Sheets

(51) Int. Cl.
    *A23B 2/729*     (2025.01)
    *A23B 2/742*     (2025.01)
    *A23B 2/762*     (2025.01)
    *A23B 2/783*     (2025.01)
    *A23B 9/26*     (2006.01)
    *A23B 9/28*     (2006.01)
    *C07C 29/80*     (2006.01)
    *C12N 1/18*     (2006.01)

(52) U.S. Cl.
    CPC .............. *A23B 2/762* (2025.01); *A23B 2/783* (2025.01); *A23B 9/26* (2013.01); *A23B 9/28* (2013.01); *C07C 29/80* (2013.01); *C12N 1/18* (2013.01); *A23V 2002/00* (2013.01); *Y02E 50/10* (2013.01)

(56) References Cited

U.S. PATENT DOCUMENTS

| | | | |
|---|---|---|---|
| 2008/0210630 A1* | 9/2008 | Whiteman | C02F 3/006 210/610 |
| 2010/0151104 A1 | 6/2010 | Smith | |
| 2010/0324137 A1* | 12/2010 | Coughlin | A01N 47/44 514/551 |
| 2016/0081354 A1 | 3/2016 | Consalo et al. | |

OTHER PUBLICATIONS

Written Opinion of the International Searching Authority for PCT/US2016/041015, dated Oct. 21, 2016 (11 pages).

* cited by examiner

Formula: $C_{33}H_{47}NO_{13}$

Structure:

METHOD AND SYSTEM FOR TREATMENT
OF MICROORGANISMS DURING
PROPAGATION, CONDITIONING,
FERMENTATION, AND PRESERVATION
USING ETHYL LAUROYL ARGINATE AND
SELECTED ADDITIVES

CROSS-REFERENCE TO RELATED
APPLICATIONS

This patent application claims the priority benefit of both U.S. Patent Application No. 62/189,146, filed on Jul. 6, 2015, for "Method and Apparatus for Treatment of Microorganisms During Propagation, Conditioning, and Fermentation Using LAE and Selected Acids", and U.S. Patent Application No. 62/197,994, filed on Jul. 28, 2015, for "Preservative for Distiller's Grain, Grain By-Products, and Processed Grain and Methods of Use". Moreover, this patent application hereby incorporates by reference U.S. Patent Application No. 62/189,146 and U.S. Patent Application No. 62/197,994, each in their entirety, for all purposes.

BACKGROUND

The present inventive disclosures relates generally to microbial control in fermentation, conditioning, and propagation processes in order to enhance production efficiencies for distillation-based alcohol products, as well as to preservation strategies of distiller's grains that result from the aforementioned processes in order to both minimize the presence of unwanted microbes while also minimizing, if not completely eliminating, the presence of undesired antibiotics within distiller's grains, which in turn are often used for livestock feed.

Distillation-Production Processes

In particular, the present inventive disclosures involve a method of reducing or controlling the concentration of undesirable microorganisms. Microorganisms, such as yeast, fungi and bacteria, are used to produce a number of fermentation products, such as industrial grade ethanol, distilled spirits, beer, wine, pharmaceuticals, and nutraceuticals (foodstuff that provides health benefits, such as fortified foods and dietary supplements), baking-industry ingredients, and industrial chemicals.

Yeast is commonly used in fermentation processes. One common type of yeast is *Saccharomyces cerevisiae*, the species predominantly used in baking and fermentation. Non-*Saccharomyces* yeasts, also known as non-conventional yeasts, are also used to make a number of commercial products. Other microorganisms can also be useful in making fermentation products. For example, cellulosic ethanol production; that is, production of ethanol from cellulosic biomass; utilize various hydrolysis methods in addition to fungi and bacteria. Examples of these cellulolytic fungi include *Trichoderma reesei* and *Trichoderma viride*. One example of a bacteria used in cellulosic ethanol production is *Clostridium ljungdahlii*.

Most of the yeast used in distilleries and fuel ethanol plants are purchased from manufacturers of specialty yeasts. The yeast is manufactured through a propagation process that involves growing a large quantity of yeast from a small lab culture of yeast. During propagation, the yeast are provided with the oxygen, nitrogen, sugars, proteins, lipids, and ions that are necessary or desirable for optimal growth through aerobic respiration.

Once at the distillery, the yeast can undergo conditioning. Conditioning is unlike propagation in that it does not involve growing a large quantity from a small lab culture. Rather, during conditioning, conditions are provided to re-hydrate the yeast, bring them out of hibernation, and allow for maximum growth and reproduction. The objective of both propagation and conditioning is to deliver a large volume of yeast to the fermentation tank with high viability, high budding, and a low level of infection by other microorganisms.

Following propagation and/or conditioning, the yeast enters the fermentation process, wherein the yeast is combined in an aqueous fluid solution with fermentable sugars. The yeast consume the sugars, converting the sugars into aliphatic alcohols, such as ethanol. The fermentation process begins with the preparation of a fermentable carbohydrate. In ethanol production, beverage alcohol production, and other advanced biofuels production, corn is one possible source of fermentable carbohydrate. Other carbohydrate sources such as cereal grains, cellulose-starch bearing materials (e.g., as wheat or milo), sugar cane, other sugars (e.g., sugars from beets, agave plants, etc.), can also be substituted. Cellulosic biomass such as straw and cornstalks can also be used. Cellulosic-ethanol production has recently received attention because it uses readily available nonfood biomass to form a valuable fuel.

The propagation, conditioning, and fermentation processes can be carried out using batch or continuous methods. The batch process is used for small-scale production, and each batch is completed before a new one begins. The continuous-fermentation method is used for large-scale production because it produces a continuous supply without restarting the process every time.

During the propagation, conditioning, or fermentation process, the mash or the fermentation mixture can become contaminated with other microorganisms, such as spoilage bacteria. These microorganisms compete with the desired species of yeast for fermentable sugars and retard the desired bio-chemical reaction resulting in a lower product yield. They can also produce unwanted chemical byproducts, which can cause spoilage of entire fermentation batches.

Producers of ethanol attempt to increase the amount of ethanol produced from one bushel of cereal grains (approximately 56 pounds [25.4 kilograms]). Contamination by microorganisms lowers the efficiency of yeast making it difficult to attain or exceed the desired industry levels of 2.8-2.9 gallons of ethanol per bushel (0.42-0.44 liters per kilogram). Reducing the concentration of undesirable microorganisms encourages yeast propagation and/or conditioning and increases yeast efficiency, making it possible to attain and exceed these desired industry production levels.

During any of the propagation, conditioning, or fermentation processes, the yeast can become contaminated with undesirable yeast, bacteria, or other undesirable microorganisms. This can occur in one of the many vessels used in propagation, conditioning, or fermentation. This includes, but is not limited to, propagation tanks, conditioning tanks, starter tanks, fermentations tanks, and the piping and heat exchangers between these units.

Bacterial or microbial contamination reduces the fermentation product yield in three main ways: First, the sugars that could be available for yeast to produce alcohol are consumed by the bacteria or other undesirable microorganisms and diverted from alcohol production, reducing yield. Second, the end products of bacterial metabolism, such as lactic acid and acetic acid, inhibit yeast growth and yeast fermentation/respiration, which also results in less efficient yeast production. Finally, the bacteria or other undesirable microorganisms compete with the yeast for nutrients other than sugar.

After the fermentation system or vessel has become contaminated with bacteria or other undesirable microorganisms, those bacteria or other microorganisms can grow much more rapidly than the desired yeast. The bacteria or other microorganisms compete with the yeast for fermentable sugars and retard the desired bio-chemical reaction resulting in a lower product yield. Bacteria also produce unwanted chemical byproducts, which can cause spoilage of entire fermentation batches. Reducing these bacteria or other undesirable microorganisms allows the desired yeast to thrive, which results in higher efficiency of production.

As little as a one-percent decrease in ethanol yield is highly significant to the ethanol-fuel industry. In larger facilities, such a decrease in efficiency will typically reduce income from 1-million to 3-million dollars per year.

Some methods of reducing bacteria or other undesirable microorganisms during propagation, conditioning, and fermentation take advantage of the higher temperature and the pH tolerance of yeast over other microorganisms. This is done by applying heat to or lowering the pH of the yeast solution. However, those processes are not entirely effective in retarding bacterial growth. Furthermore, the desirable yeast microorganisms, while surviving, are stressed under the higher temperatures and/or lower pH levels and as a result are not as vigorous or healthy. Thus, the yeasts do not perform as well.

The predominant trend in the ethanol industry is to reduce the pH of the mash (feed stock) to less than 4.5 at the start of fermentation. Lowering the pH of the mash reduces the population of some species of bacteria. However, this method is much less effective in reducing problematic bacteria, such as lactic-acid producing bacteria. This method also significantly reduces ethanol yield by stressing the yeast used for ethanol production.

Another approach involves washing the yeast with phosphoric acid. However, this method does not effectively kill bacteria and other microorganisms, and can also stress the yeast used for ethanol production, thereby lowering their efficiency.

Yet another method is to use heat or harsh chemicals to sterilize process equipment between batches, though this method is ineffective at killing bacteria and other microorganisms within the yeast mixture during production.

In still another method, antibiotics are added to yeast propagation, conditioning, or fermentation batch to neutralize unwanted bacteria. Fermentation industries typically apply antibiotics to conditioning, propagation, and fermentation processes. Overall antibiotic dosage rates range between 0.1 to 1.0 mg/L and can exceed 20 mg/L in specific plant processes. However, problems exist with using antibiotics in conditioning, propagation, and fermentation in that antibiotics are expensive and can add greatly to the costs of large-scale production. Moreover, antibiotics are not effective against all strains of bacteria, such as antibiotic-resistant strains of bacteria. Further, the overuse of antibiotics can lead to the creation of additional variants of antibiotic-resistant strains of bacteria. Consumer demand for antibiotic-free protein is clearly evident.

Antibiotic residues and establishment of antibiotic-resistant strains is a global issue. These concerns may lead to future regulatory action against the use of antibiotics. One area of concern is distillers grains that are used for animal feed. Distillers grain is the grain residue of the fermentation process. European countries do not allow the byproducts of an ethanol plant to be sold as animal feed if antibiotics are used in the facility. Distiller grain sales account for up to 25% of an ethanol plant earnings. Antibiotic concentration in the byproduct can range from 1-3% by weight, thus negating this important source of income.

In addition, there are other issues to consider when using antibiotics. Mixtures of antibiotics should be frequently balanced and changed in order to avoid single uses that will lead to antibiotic-resistant strains. Sometimes the effective amount of antibiotic cannot be added to the fermentation mixture. For example, utilizing over 6 mg/L of Virginiamycin will suppress fermentation, but over 25 mg/L is required to inhibit grown of *Weisella confusa*, an emerging problematic bacteria strain. Overdosing or overuse of antibiotic can stress yeast and impact efficiency and/or cause regulatory non-compliance.

Industries that employ fermentation for beverages have historically applied hops acid to propagation and fermentation to control unwanted microbes that compete with the yeast for nutrients. With the recent expansion of fuel ethanol demand and production, hops acids have been utilized to a minor degree to address unwanted microbes. Competition between yeasts and unwanted microbes results in yield loss of fuel ethanol as unwanted microbes, primarily *Lactobacillus* and *Acetobacter*, reduce the efficiency of fermentation. In beverage production, competing microbes not only reduce efficiency but can alter the aesthetics and taste of the final product.

Organic acids have many applications, including being used as acidifiers, buffers, antioxidants, chelators, synergists, dietary supplements, flavoring agents, preservatives, and antimicrobials. Organic acids have been used as preservatives because of their effect on bacteria. The mode of action of organic acid is that the non-dissociated acids penetrate the bacterial cell wall via passive diffusion and disrupt the normal physiology of the cell in two ways: The acids dissociate and therefore lower the internal pH, which is normally close to neutral, impairing the function of the bacteria. The anionic part of the acid that is unable to leave the cell in its dissociated form accumulates within, disrupting metabolic functions and increasing osmotic pressure.

Since small decreases in ethanol yield are highly significant to the fuel ethanol industry, ethanol producers are constantly looking for ways to increase efficiency.

Antimicrobials are used to eliminate, reduce, or otherwise control the number of competing bacteria in the aqueous systems. However, the use of antimicrobials will always add cost to operations and products and thus more effective ways to achieve microbial control are sought. In addition, some antimicrobials may have deficiencies in either their spectrum of antimicrobial action or operational limitations in their manner of application, such as lack of temperature stability or susceptibility to inactivation by environmental or chemical factors.

Accordingly, there is a need to develop an effective and economical means to ensure healthy yeast growth and resultant effective fermentation processes while also minimizing or eliminating the introduction of artificial antibiotics within both the distillation products and any associated byproducts that may be used for other purposes, such as animal feed.

Distiller's-Grain Preservation

Further, the present inventive disclosures also relates generally to preservatives for grain products having a high water activity or moisture content and, more specifically, Lauryl-L-arginine ethyl ester monohydrochloride (aka "Lauric arginate" or "LAE"), with or without a blend of one or more organic acids, that is effective at preserving ordinarily highly perishable high-moisture grain products.

Today's agricultural commodities are widely used as starting materials in a variety of manufacturing processes; for example, manufacturing of high-fructose corn syrup, fermentation of alcohols, extraction of sugars, citrus-juice production, extraction of oils, and the like. A byproduct of many such processes is a high-moisture, high-fiber organic material. Such materials have potential commercial value—often as feedstuffs for ruminant animals—but are not fully exploited due to their highly perishable nature. Distiller's grain feed is a good example. A large amount of distiller's grain is produced as a byproduct of ethanol processing; the U.S. domestic market is estimated at 40 million tons per year. Distiller's grain is a suitable and primary component in dairy, beef (cattle), poultry, swine and aquaculture rations.

Unfortunately, wet distiller's grain (WDG) will become unpalatable due to spoilage if not fed within one to seven days. This limits the market for wet distiller's grains and like products to those facilities located within a close radius of the processing facility that permits loading, shipment, and feeding of the wet distiller's grain within the short "shelf life" of the product. The U.S. distiller's-grain market would be substantially expanded and production cost substantially reduced if the product could be preserved for seven to 21 days, or more, and the export market could be enhanced by such an extended shelf life as well. However, the industry currently has no known method of preservation is known to exist which extends the shelf life of the product to this extent. Further, the use of any type of antibiotics in the production and/or preservation of distiller's grains has the potential of introducing many undesirable effects within food supplies, as discussed supra.

Accordingly, there is a need to develop an effective and economical preservative or stabilization agent for high-moisture organic materials, particularly for wet distiller's grains, while also keeping end-products made from said high-moisture organic materials free (or substantially free) of man-made antibiotics.

BRIEF SUMMARY

Some of the inventive disclosures presented herein are directed generally to a process for improving yeast conditioning and propagation, leading to improved fermentation processes and yields. In one embodiment, solutions containing yeast are introduced to an effective amount of Lauryl-L-arginine ethyl ester monohydrochloride (aka "Lauric arginate" or "LAE") to inhibit the population of competing bacteria and other undesired microorganisms without having to use antibiotics. In a variation, the yeast solution is also exposed to an effective amount of hops acid and/or organic acids in conjunction with the LAE. However, in the present inventive processes disclosed, hops acid is not used in conjunction with LAE for the purposes of being a distiller's grain preservative.

Extensive testing using LAE-based fermentation systems versus control systems that used traditional antibiotics such as Virginiamycin, which is generally considered the "gold standard" in the industry for its ability to reduce Gram-positive bacteria in ethanol fermentations, statistically revealed that the LAE-based additives worked just as well in fighting the growth of unwanted microbes while yielding antibiotic-free ethanol products. In addition, the testing also revealed that LAE-based additives slightly outperformed both Isoalpha hops acid and Virginiamycin in the reduction of Gram-negative bacteria. Moreover, LAE-based fermentation systems resulted in lower Glycerol production, which in turn appeared to allow yeast to propagate and thrive better, as opposed to fermentation systems that relied on Virginiamycin and/or Isoapha hops acid.

In addition, some of the inventive disclosures presented herein are directed generally to a preservative comprised of LAE for grain products having a high water activity or moisture content, which in some variations is also blended with one or more organic acids. In one embodiment, the organic acids are selected from the group consisting of propionic acid, benzoic acid, citric acid, phosphoric acid, and sorbic acid. Preservatives based only on LAE and preservatives based on LAE combined with organic acid(s) are efficacious. The rate of preservative application is dependent on the material being treated. In an embodiment, the LAE-based preservative is applied at a rate of between about 2 lbs. and about 50 lbs. per ton of distiller's grain, and the organic acid(s) is included at a rate of between approximately 0.0005% and approximately 0.70% by weight. The positive results of the aforementioned processes include enhanced production yields of ethanol without the use of antibiotics and also improved product-by-process in the form of distiller's grains that are substantially antibiotic-free, which in turn can be safely introduced into food supplies by way of the use of the distiller's grains in animal feed. Of course, the inclusion rate will also depend on the length of time that a storage facility desires to extend the shelf life.

Materials having characteristics that make them suitable for preservation by the present inventive disclosures include organic materials that have a total moisture content of >10% and water activity ($A_w$) that supports the growth of molds, yeasts, and/or gram-positive/gram-negative bacteria. While some microbes, such as *Clostridium botulinum*, stop growing at a water activity $A_w$<0.95 (<95% water), yeasts and molds will continue to grow at a water activity $A_w$ of as little as 0.7 to 0.75. Most pathogenic aerobic bacteria stop growing at a water activity $A_w$ of around 0.90. Commercial grain products having these characteristics include wet-corn gluten feed, wet/dry distiller's grains, fuzzy cottonseed, wet and dry brewer's grains, cottonseed meal, corn hominy feed, almond hulls, wet and dry sugar beet pulp, canola meal, citrus pulp, rice bran, safflower meal, soybean hulls, food-processing waste, and wheat-mill run. Of course, a great many other products have such characteristics, including many food products.

Overall, laboratory testing data indicates that LAE, as an additive to fermentation systems, can compete as an antibiotic-free substitute for traditional antibiotics used for combating unwanted microbial growth/bacterial infections. The primary advantages to using LAE-based additives include the following: (a) LAE is safer in distiller's grains at inclusion levels much higher (up to 173 ppm) than those used for traditional antimicrobial additives such as Virginiamycin (up to 1 ppm); (b) LAE is much more economical to use than hops-acid additives such as Isoalpha hops acid; and (c) unlike traditional additives like Virginiamycin and Isoalpha hops acid, LAE is also effective against Gram-negative bacteria and molds.

The foregoing Brief Summary is intended to merely provide a short, general overview of the inventive disclosures described throughout this patent application, and therefore, is not intended to limit the scope of the inventive disclosure contained throughout the balance of this patent application, including any appended Claims, Drawings, and appendices.

BRIEF DESCRIPTION OF THE DRAWINGS

FIG. 2B provides a visual depiction of test data relating to ethanol output from corn-mash fermentations challenged with bacterial contamination and treated with 35 ppm LAE or 5 ppm Lactocide V (Virginamycin) (at the same time as the introduction of the bacteria), with the results being the averages of triplicate samples (within one standard deviation). FIG. 2C provides a visual depiction of test data relating to ethanol output from corn-mash fermentations challenged with bacterial contamination and treated with 50 ppm LAE or 5 ppm Lactocide V (Virginamycin) (at the same time as the introduction of the bacteria), with the results being the averages of triplicate samples (within one standard deviation). FIG. 2D provides a visual depiction of test data relating to colony-forming units (CFUs) of commercial yeast preparation with bacterial-contamination growth under batch-propagation conditions (molasses) with the addition of 0 ppm, 25 ppm, or 50 ppm LAE.

DETAILED DESCRIPTION

I. Terminology

Figure 1:
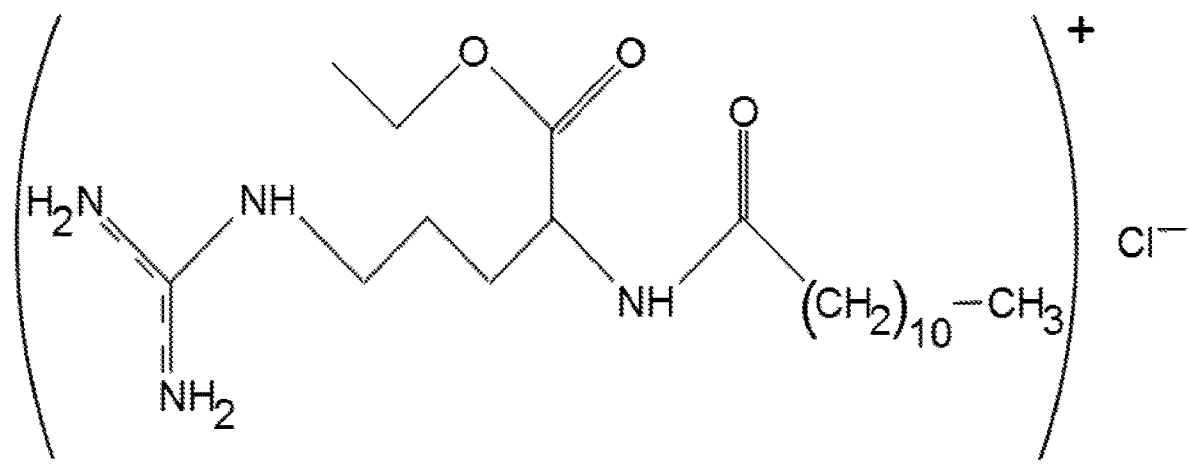
FIG. 1 depicts both the chemical formula and the molecular structure of Lauryl-L-arginine ethyl ester monohydrochloride; aka "Lauric arginate"; aka "LAE".

The terms and phrases as indicated in quotes (" ") in this Section I are intended to have the meaning ascribed to them in this Terminology Section applied to them throughout this document, including the Claims, unless clearly indicated otherwise in context. Further, as applicable, the stated definitions are to apply, regardless of the word or phrase's case, to the singular and plural variations of the defined word or phrase.

The term "or", as used in this Specification and the appended Claims, is not meant to be exclusive; rather, the term is inclusive, meaning "either or both".

References in the Specification to "one embodiment", "an embodiment", "a preferred embodiment", "an alternative embodiment", "a variation", "one variation", and similar phrases mean that a particular feature, structure, or characteristic described in connection with the embodiment is included in at least an embodiment of the invention. The appearances of the phrase "in one embodiment" and/or "in one variation" and similar phrases in various places in the Specification are not necessarily all meant to refer to the same embodiment.

The term "couple" or "coupled", as used in this Specification and the appended Claims, refers to either an indirect or a direct connection between the identified elements, components, or objects. Often the manner of the coupling will be related specifically to the manner in which the two coupled elements interact.

The term "removable", "removably coupled", "readily removable", "readily detachable", "detachably coupled", and similar terms, as used in this Specification (including the Claims and Drawings), refer to structures that can be uncoupled from an adjoining structure with relative ease (i.e., non-destructively and without a complicated or time-consuming process) and that can also be readily reattached or coupled to the previously adjoining structure.

Directional and/or relational terms such as, but not limited to, left, right, nadir, apex, top, bottom, vertical, horizontal, back, front, lateral, proximal, and distal are relative to each other, are dependent on the specific orientation of an applicable element or article, are used accordingly to aid in the description of the various embodiments, and are not necessarily intended to be construed as limiting in this Specification and the appended Claims.

As applicable, the terms "about" or "generally", as used herein unless otherwise indicated, means a margin of +−20%. Also, as applicable, the term "substantially" as used herein unless otherwise indicated means a margin of +−10%. It is to be appreciated that not all uses of the above terms are quantifiable such that the referenced ranges can be applied.

The term "ppm", as used in this Specification (including the Claims and Drawings), is measured as mass per volume; e.g., 1 ppm equals 1 mg (active) per liter.

The term "dosage", as used in this Specification (including the Claims and Drawings), is defined as the concentration of the component in the system being treated.

The terms "hops acid" and "hops-acid extract", as used in this Specification (including the Claims and Drawings), are used interchangeable. Further, references to "hops acid" or "hops-acid extract" can include, but is not limited to, any one or combination of the following hops-acid types: Iso-Alpa, Beta, Tetra Iso, and Hexa Iso.

The term "organic acid", as used in this Specification (including the Claims and Drawings), also refers to the organic acid's salt. For example, when the term citric acid is used it includes the salt form of citric acid, which is a preferred type of organic acid used herein, though other organic acids can be used. Any reference to an organic acid includes reference to its salt.

The term "Lauryl-L-arginine ethyl ester monohydrochloride" as used in this Specification (including the Claims and Drawings), is interchangeable with the terms "Lauric arginate" and "LAE". LAE is an antimicrobial of the cationic surfactant, and its chemical expression is $C_{33}H_{47}NO_{13}$. FIG. 1 depicts LAE's molecular structure. LAE is synthesized by esterifying arginine with ethanol, followed by reacting the ester with lauroyl chloride. The resultant ethyl lauroyl arginate is recovered as hydrochloride salt and is a white, solid product which is filtered off and dried. Some commercial names for LAE include, "LAEPro™" and "LAEPro™ S50", produced by ChiHonBio, and MIRENAT®-P/100 and MIRENAT®-GA, produced by Vedeqsa, Inc. Other synonyms for LAE used in the art include "Lauric arginate ethyl ester", "lauramide arginine ethyl ester", and "ethyl-Na-lauroyl-L-arginate·HCl". LAE exhibits a wide spectrum of activity against Gram-positive and Gram-negative bacteria, yeasts, and molds across a wide range of pH levels (i.e., 3-9 pH). Moreover, LAE was affirmed as GRAS (generally recognized as safe) by the U.S. Food & Drug Administration (FDA) in 2005, and as a food preservative by the European Food Safety Authority (EFSA) in 2007. LAE is often used for ready-to-eat (RTE) meat and poultry products, with a normal dosage is between 50 and 200 ppm.

The term "surfactant" as used in this Specification (including the Claims and Drawings), refers to any compound that lowers the surface tension (or interfacial tension) between two liquids or a liquid and a solid. In various industries, surfactants are primarily and typically used as constituents of detergents, wetting agents, emulsifiers, foaming agents, and dispersants.

The term "water activity", as used in this Specification (including the Claims and Drawings), and typically represented as either "A.sub.w" or "$A_w$," herein, is a food-science term that is defined as the partial vapor pressure of the water content in a substance at a given temperature divided by the partial vapor pressure of pure water at the same given temperature. Higher water activity values in a substance typically implicate higher microorganism growth rates in the substance (there are some exceptions to this general rule for substances containing crystalline salt or sugar). The value of water activity is a ratio that will range from 0.0 to 1.0, with 1.0 representing pure water.

II. Laboratory Testing Supporting the Use of LAE as an Antimicrobial Agent

The inventive disclosures presented in this Section II are directed generally to experimental studies conducted to assess the viability of inhibiting the growth of unwanted microbes during yeast conditioning and propagation, leading to improved fermentation processes and yields, as well as to substantially antibiotic-free byproduct solids. In typical experiments, solutions containing yeast are introduced to an effective amount of Lauryl-L-arginine ethyl ester monohydrochloride (aka "Lauric arginate" or "LAE") to inhibit the population of competing bacteria and other undesired microorganisms without having to use antibiotics. In variations, the yeast solution is also exposed to an effective amount of hops acid and/or organic acid in conjunction with the LAE.

LAE was selected as a potential effective agent to efficiently and safely eliminate unwanted microorganisms because it exhibits a wide spectrum of activity against Gram positive and negative bacteria, yeasts, and molds across a wide range of pH levels (i.e., 3-9 pH), while simultaneously supporting yeast vitality. LAE has exhibited safe biocidal properties, even though LAE was originally developed as a surfactant. LAE, as a surfactant, also inhibits the growth of unwanted microbes by reducing aqueous surface tension and thus the partial vapor pressure or water activity ($A_w$) within the materials in which LAE is applied. This, in turn, typically corresponds to inhibited growth of unwanted microbes within the materials, and also potentially disrupts the cell outer membranes of some unwanted microbes. Moreover, LAE was affirmed as GRAS (generally recognized as safe) by FDA in 2005, and as a food preservative by the European Food Safety Authority (EFSA) in 2007. LAE is often used for ready-to-eat (RTE) meat and poultry products, with a normal dosage is between 50 and 200 ppm.

LAE has been proven to exhibit antimicrobial efficacy against *E. Coli, Salmonella typhimurium; Listeria monocyt; Campylobacter; Lactobacillus; Aspergillus niger*; and other bacteria, molds and specific yeasts. LAE offers a relatively long shelf life compared to many other compounds, is considered a very safe compound; is rapidly metabolized into natural endogenous compounds; exhibits no organoleptic changes; and is not pH or temperature dependant. LAE is considered "food-grade" and meets Food & Agriculture Organization of the United Nations (FAO) and World Health Organization (WHO) specifications and complies with applicable US Code of Federal Regulations. In some embodiments, LAE is soluted in the aforementioned aqueous system at a 3-5 pH.

In support of validating LAE, High Performance Liquid Chromatography (HPLC) was used in a first phase of testing to evaluate the effects of LAE applications at various concentrations in order to determine the minimal inhibitory concentrations (MIC) of the LAE antimicrobial on a panel of industry-relevant bacteria. Refer to Tables 1 and 2 below, as well as FIGS. 2A-2D.

TABLE 1

Minimal Inhibitory Concentrations (MIC) of the LAE Antimicrobial on a Panel of Industry-Relevant Bacteria

| | Bacteria Strain | | | | |
|---|---|---|---|---|---|
| | *Lactobacillus fermentum* | *Lactobacillus Brevis* | *Lactobacillus plantarum* | *Pediococcus acidilactici* | *Gluconobacter cerinus* |
| MIC (ppm) | 15 | 20 | 40 | 35 | 25 |

Figure 2A:
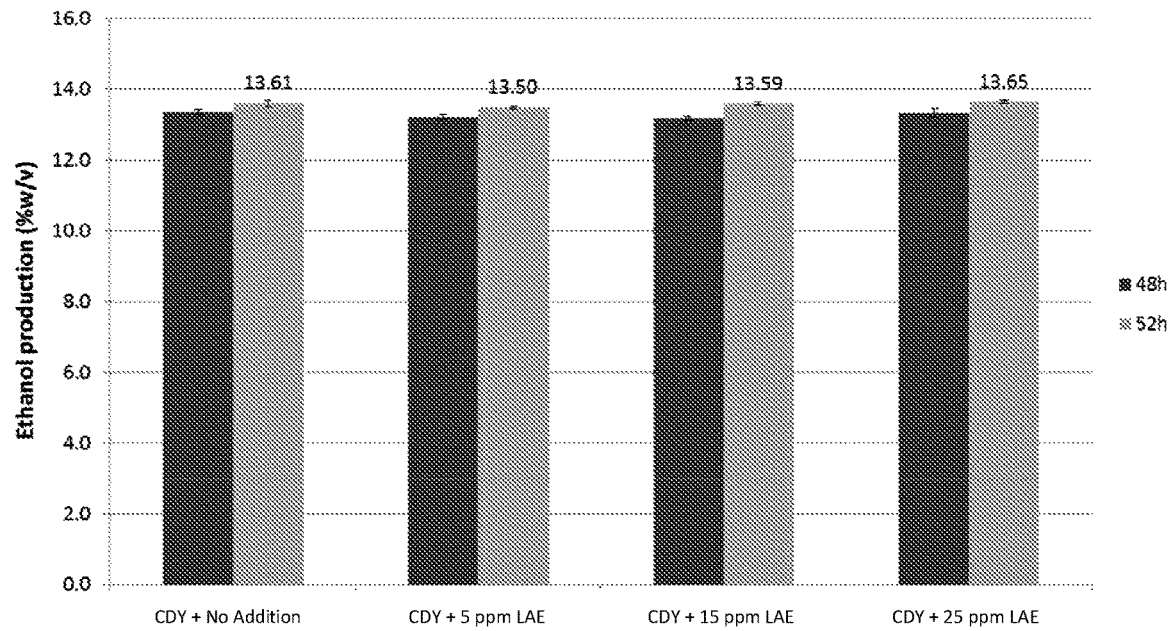
FIGS. 2A-2D depict one set of experimental data for LAE antimicrobial characterization. Specifically, FIG. 2A provides a visual depiction of test data relating to ethanol output from corn-mash fermentations treated with varying concentrations of LAE, with the results being the averages of triplicate samples (within one standard deviation).
Figure 2B:
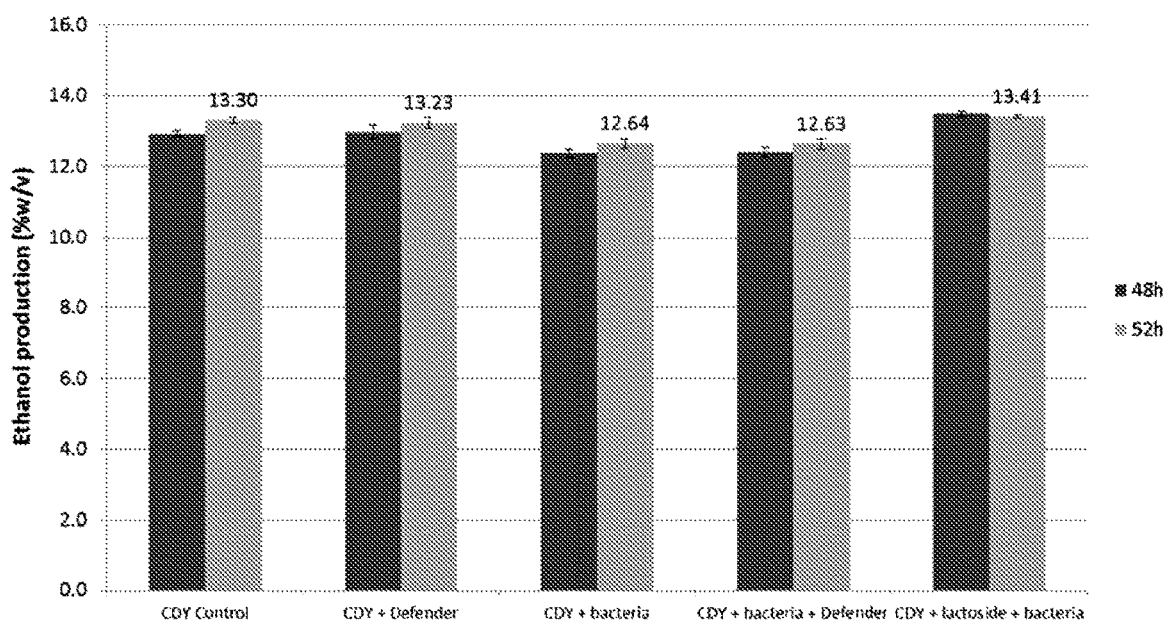
Figure 2C:
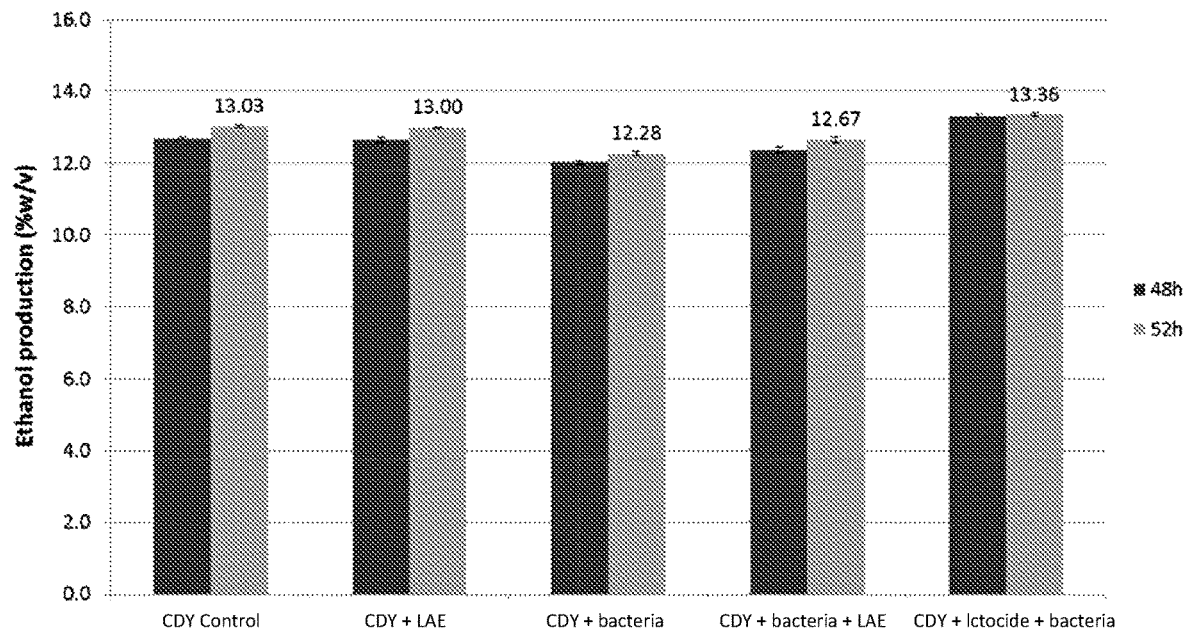
Figure 2D:
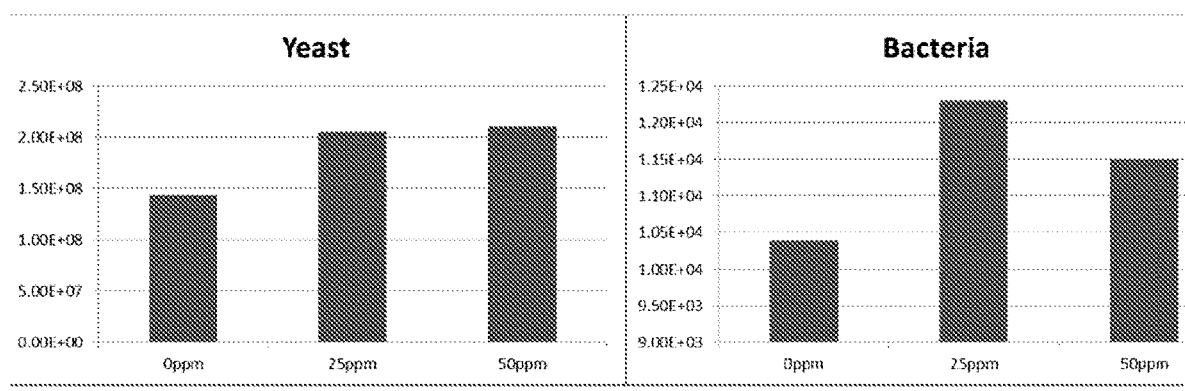

FIG. 2A provides a visual depiction of test data relating to ethanol output from corn-mash fermentations treated with varying concentrations of LAE, with the results being the averages of triplicate samples (within one standard deviation). FIG. 2B provides a visual depiction of test data relating to ethanol output from corn-mash fermentations challenged with bacterial contamination and treated with 35 ppm LAE or 5 ppm Lactocide V (Virginamycin) (at the same time as the introduction of the bacteria), with the results being the averages of triplicate samples (within one standard deviation). FIG. 2C provides a visual depiction of test data relating to ethanol output from corn-mash fermentations challenged with bacterial contamination and treated with 50 ppm LAE or 5 ppm Lactocide V (Virginamycin) (at the same time as the introduction of the bacteria), with the results being the averages of triplicate samples (within one standard deviation). FIG. 2D provides a visual depiction of test data relating to colony-forming units (CFUs) of commercial yeast preparation with bacterial-contamination growth under batch-propagation conditions (molasses) with the addition of 0 ppm, 25 ppm, or 50 ppm LAE.

TABLE 2

HPLC Results from Corn-Mash Fermentations Challenged With Bacterial Contamination and LAE Treatments

| | Average (% wt/vol) | | | | | | | |
|---|---|---|---|---|---|---|---|---|
| | DP4 | DP3 | Maltose | Glucose | Lactic Acid | Glycerol | Acetic Acid | Ethanol |
| Culture Dry Yeast (CDY) Control | 0.87 | 0.14 | 0.44 | 0.74 | 0.45 | 1.53 | 0.18 | 13.03 |
| CDY + LAE | 0.87 | 0.14 | 0.44 | 0.83 | 0.44 | 1.51 | 0.18 | 13.00 |
| CDY + Bacteria | 0.93 | 0.15 | 0.48 | 1.52 | 0.89 | 1.66 | 0.15 | 12.28 |
| CDY + LAE + Bacteria | 0.87 | 0.14 | 0.46 | 1.20 | 0.63 | 1.52 | 0.17 | 12.67 |
| CDY + Lactocide + Bacteria | 0.78 | 0.15 | 0.48 | 0.12 | 0.27 | 1.59 | 0.14 | 13.36 |

One of the primary goals with the first phase of the LAE studies was to determine whether the addition of LAE would adversely affect ethanol production, and it was determined that LAE not only was not harmful to ethanol-production processes, but that unwanted microbe growth was inhibited using LAE enough to allow foregoing the use of antibiotics. Part of this analysis was to determine whether the introduction of LAE into the ethanol-production process would adversely impact the stillage byproducts used in animal feed, and for that matter whether the further use of LAE as a preservative in such byproducts would be safe for consumption by agricultural livestock. The general conclusion was that such LAE-exposed byproducts of the ethanol-production process and/or distiller's grains are generally recognized as safe (GRAS) safe. The testing serving as a basis for this conclusion assumed a maximum residual concentration of the LAE of 173 ppm in the distiller's grains. The safety of distiller's grains with LAE concentrations above 173 ppm was not fully evaluated.

Further studies were commissioned at Iowa State University in which yeast was propagated at a temperature of 31° C. and yeast budding, cell counts, and viability were measured just after seven hours of propagation activity, and then again at the 63-hour mark. Similarly, HPLC data was taken at the seven-hour mark and at the 63-hour mark to measure parameters indicative of the degree of polymerization, enzyme profiles, and of yeast stress. Tables 3-6 summarize the test results:

TABLE 3

Yeast Counts Propagated for 7 Hours at 31° C.

| | Budding (%) | Cell Count | Viability (%) |
|---|---|---|---|
| Control | 16.5 | 206 | 94 |
| 10 ppm LAE | 25.71 | 175 | 94 |
| 20 ppm LAE | 15.33 | 261 | 96 |
| 50 ppm LAE | 13.54 | 192 | 91 |

TABLE 4

HPLC for Yeast Counts Propagated for 7 Hours at 31° C. (% wt/wt)

| | DP4+ | DP3+ | DP2+ | Dextrose | Succinic Acid | Lactic Acid | Glycerol | Acetic Acid | Ethanol |
|---|---|---|---|---|---|---|---|---|---|
| Control | 5.906 | 0.505 | 3.367 | 6.100 | 0.075 | 0.141 | 0.796 | 0.035 | 2.018 |
| 10 ppm LAE | 5.838 | 0.456 | 3.353 | 6.199 | 0.074 | 0.140 | 0.795 | 0.033 | 2.026 |
| 20 ppm LAE | 5.784 | 0.393 | 3.326 | 6.285 | 0.073 | 0.138 | 0.791 | 0.034 | 2.042 |
| 50 ppm LAE | 5.721 | 0.350 | 3.313 | 6.391 | 0.074 | 0.138 | 0.795 | 0.033 | 2.022 |

TABLE 5

Yeast Counts Propagated for 63 Hours at 31° C.

| | Budding (%) | Cell Count | Viability (%) |
|---|---|---|---|
| Control | 0.96 | 104 | 57 |
| 10 ppm LAE | 2.65 | 264 | 58 |
| 20 ppm LAE | 2.21 | 226 | 63 |
| 50 ppm LAE | 13.46 | 260 | 65 |

TABLE 6

| | DP4+ | DP3+ | DP2+ | Dextrose | Succinic Acid | Lactic Acid | Glycerol | Acetic Acid | Ethanol |
|---|---|---|---|---|---|---|---|---|---|
| Control | 1.111 | 0.084 | 0.447 | 0.027 | 0.177 | 0.046 | 1.777 | 0.048 | 12.843 |
| 10 ppm LAE | 1.125 | 0.100 | 0.469 | 0.038 | 0.174 | 0.047 | 1.761 | 0.046 | 12.885 |
| 20 ppm LAE | 1.244 | 0.069 | 0.424 | 0.033 | 0.176 | 0.041 | 1.802 | 0.050 | 12.539 |
| 50 ppm LAE | 1.248 | 0.077 | 0.424 | 0.039 | 0.175 | 0.041 | 1.782 | 0.048 | 12.552 |

HPLC for Yeast Counts Propagated for 63 Hours at 31° C. (% wt/wt)

As a result of the above-discussed testing, it was determined that in most applications, the recommended concentration of LAE in the yeast conditioning, propagation, and fermentation solutions is 5-75 ppm, with 35 ppm generally being a preferred concentration.

The extensive testing using LAE-based fermentation systems versus control systems that used traditional antibiotics such as Virginiamycin, which is generally considered the "gold standard" in the industry for its ability to reduce Gram-positive bacteria in ethanol fermentations, statistically revealed that the LAE-based additives worked just as well in fighting the growth of unwanted microbes while yielding antibiotic-free ethanol products an byproducts (such as distiller's grains). In addition, the testing also revealed that LAE-based additives slightly outperformed both Isoalpha hops acid and Virginiamycin in the reduction of Gram-negative bacteria. Moreover, LAE-based fermentation systems resulted in lower Glycerol production, which in turn appeared to allow yeast to propagate and thrive better, as opposed to fermentation systems that relied on Virginiamycin and/or Isoapha hops acid.

Overall, laboratory testing data indicates that LAE, as an additive to fermentation systems, can compete as an antibiotic-free substitute for combating unwanted microbial growth/bacterial infections. Moreover, powdered LAE compositions took much longer to solubilize than did liquid formulations of LAE. In addition, powdered formulations of LAE we observed to attach to starch molecules due to the polarity of LAE molecules, which is not desirable.

The primary advantages to using LAE-based additives include the following: (a) LAE is safer in distiller's grains at inclusion levels (up to 173 ppm) much higher than those used for traditional antimicrobial additives such as Virginiamycin (up to 1 ppm); (b) LAE is much more economical to use than hops-acid additives such as Isoalpha hops acid; and (c) unlike traditional additives like Virginiamycin and Isoalpha hops acid, LAE is also effective against Gram-negative bacteria and molds.

III. An Improved Process and System for Optimizing and Enhancing Yeast Conditioning, Propagation, and Fermentation Yields The inventive disclosures presented in this Section III are directed generally to a process and associated systems for improving yeast conditioning and propagation, leading to improved fermentation processes and yields. In one embodiment, solutions containing yeast are introduced to an effective amount of Lauryl-L-arginine ethyl ester monohydrochloride (aka "Lauric arginate" or "LAE") based on the teachings of Section II, supra, to inhibit the population of competing bacteria and other undesired microorganisms without having to use antibiotics. In a variation, the yeast solution is also exposed to an effective amount of hops acid and/or organic acid in conjunction with the LAE.

In an embodiment, the combination of LAE and hops/organic acids are used in yeast conditioning, propagation, and fermentation systems and processes to take advantage of the synergies between the two substances being used simultaneously in such an application. The combination of these products provides a powerful, non-antibiotic, antimicrobial treatment. In variations, only LAE is used. LAE, either by itself, or in combination with hops acids and/or organic acids (preferably citric acid), can be used for reducing undesirable microorganism concentration, promoting desirable microorganism propagation, and increasing desirable microorganism efficiency in an aqueous system.

In some embodiments, a basic method of controlling undesirable microorganism concentration in an aqueous system employed in a fermentation process comprises the steps of: (a) Introducing a fermentable carbohydrate to an aqueous system; (b) Introducing at least one yeast to said system; (c) Introducing a hops-acid extract and/or organic acid into said system; and (d) Introducing LAE into said aqueous system. In variations, LAE is used without the use of hops-acid extract and/or organic acid. The reduction of residual byproducts of antibiotic in a fermentation process can be achieved by using the methods described herein. When using the inventive methods described herein, little or even no added antibiotics are required to be used in the fermentation process resulting in less undesired byproducts being produced and more desirable/useful byproducts being produced.

Figure 3A:
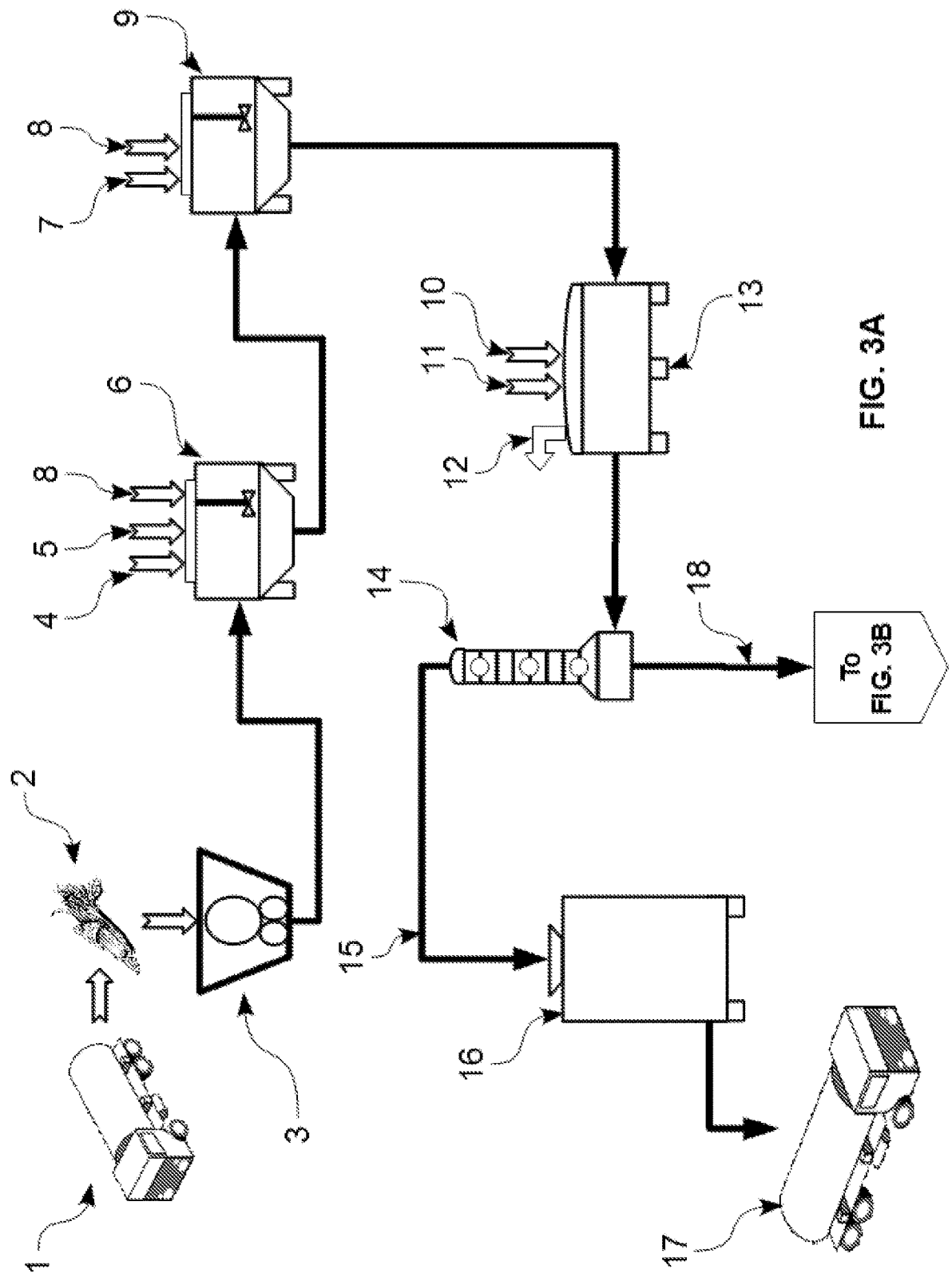
FIG. 3A depicts one embodiment of the propagation, conditioning, and fermentation process for the distillation-process production of alcohol-based products (e.g., ethanol, beverage alcohol, etc.), leaving whole stillage as a byproduct for potentially further processing, such as that depicted, for example, in FIG. 3B.

Refer to FIGS. 3A-2B. In some embodiments, a method of controlling undesirable microorganism concentration in an aqueous system employed in a fermentation process comprises the steps of:

Delivering 1 a fermentable carbohydrate 2 (e.g., corn or other grains, sugars, etc.) to a fermentation-process facility;

Introducing said fermentable carbohydrate 2 to a milling system 3 and milling to create particle sizes suitable for making mash;

Prepare 6 mash by mixing said milled fermentable carbohydrate 2 with water 4 and yeast 5 in order to create mash;

Condition 9 said mash by adding enzymes 7 and LAE 8 and allow time to for yeast to propagate;

Transfer mash to fermentation tank 13 and add more enzymes 10 and more LAE 11, allowing $CO_2$ gas to be vented off 12;

Distill 14 said fermented mash, and capture ethanol 15 into storage tank 16;

Transfer 17 ethanol 15 as required to fuel processors/end users;

Transfer whole stillage byproducts (e.g., distiller's grains) 18 to decanter 19 to separate most solids (e.g., wet grains) 24 from thin stillage 20;

Transfer thin stillage 20 to evaporator 21 to release most moisture to vapor, then transfer the resultant syrup 23 (e.g., corn oil) to storage 25;

Transfer wet grains/solids 24 to storage 25;
From storage 25, transfer wet distiller's grains and solubles 30 to end users/processors 31;
From storage 25, subject wet distiller's grains and solubles 26 to drying process 27; and
Transfer distiller's grains and solubles 28 to end users/processors 29.

Persons having ordinary skill in the art will appreciate that some of the above method steps are not required in all embodiments, depending on whether there is a desire to further process byproducts from the ethanol-production process. Moreover, the steps of the aforementioned methods/processes can be performed sequentially or in a different order. The LAE 8 and hops acids/organic acids and/or enzymes can be brought into contact with the yeast or with the fermentation carbohydrate or the yeast and the fermentable carbohydrate can be combined and then the LAE 8 and hops acid/organic acid can be introduced into the combination of yeast 5 and carbohydrate 2. The hops-acid extract 7 and/or organic acid 7 and the LAE 8 can be blended together and then added to the aqueous system 3, or they can be added separately to the aqueous system 3. The aqueous system 3 can be in a continuous process or may be a tank 6, 9, 13 in the case of a batch process.

In the foregoing method, the "undesirable" microorganisms intended to be reduced are those that compete for nutrients with the desirable microorganisms that promote the desired fermentation processes. Unwanted or undesirable microbes in fermentation include the lactic-acid-producing bacteria (LAB) and the acetic-acid-producing bacteria of which *Lactobacillus* and *Acetobacter* are prominent representatives. Any microbe that competes for the fermentable substrate 2, denying it to the intended fermenting organism 5 and thus reducing yields, can be considered undesirable. In this regard, the LAE 8 and hops-acid extract 7 and/or organic acid 7 employed in the present method do not detrimentally affect the growth and viability of desirable, fermentation-promoting microorganisms, but does eliminate or suppress the growth of undesirable microorganisms that interfere with the fermentation process. Moreover, the elimination or suppression of undesirable microorganisms has a favorable effect on the growth and viability of desirable microorganisms.

In many embodiments, the pH of the aqueous system to be treated is generally is from 3 to 11, or from 3 to 7, or from 4 to 9, or from 4 to 8, or from 4 to 6.5, or from 4.5 to 6. In general, the LAE compounds 8 work best in systems where the pH of the system is between 3 and 7, though LAE 8 can be employed in systems with pH as high as 9.

Suitable, non-limiting examples of LAE compounds 8 useful in the present inventive disclosures include, but are not limited to, "LAEPro™" and "LAEPro™ S50", produced by ChiHonBio, and MIRENAT®-P/100 and MIRENAT®-GA, produced by Vedeqsa, Inc.

In other embodiments, non-limiting examples of hops acids 7 that can be used in conjunction with the inventive disclosures herein include, but are not limited to, beta acid compounds, alpha acids, isomerized alpha acids, rho isomerized alpha acids, tetra isomerized alpha acids, hexa isomerized alpha acids, and hop leaf. In variations, hops-acid extract 7 dosages in the aqueous system being treated can be in any of the following ranges: 0.5 ppm to 120 ppm; 1 ppm to 100 ppm; 2 ppm to 70 ppm; 5 ppm to 50 ppm; 5 ppm to 45 ppm; ≥0.5 ppm; 2 ppm to 15 ppm; 5 ppm to 15 ppm; or 5 ppm to 10 ppm. In some additional non-limiting embodiments, the synergistic solution is comprised of hops-acid extracts 7 and LAE 8 in one of the following ratios: 1:10 to 1:6500; 1:15 to 1:6400; 1:20 to 1:6400; 1:20 to 1:1600; 1:25 to 1:500; 1:25 to 1:100; or 1:10 to 1:200.

In other embodiments, non-limiting examples of organic acids 7 that can be used in conjunction with the inventive disclosures herein include, but are not limited to, citric acid, benzoic acid, propionic acid, tartaric acid, acetic acid, benzenesulfonic acid, oxalic acid, malic acid, salicylic acid, lactic acid gluconic acid, hydroxyacetic acid, and their respective salts. For purposes of this disclosure, organic acid is not a hops acid. Citric acid, benzoic acid, propionic acid are preferred acids, and citric acid is the most preferred acid to use.

The LAE 8 and hops acids/organic acids 7 can be added in single or multiple locations in the fermentation process, including the slurry tank(s), cookers, mash coolers, propagators, and fermentation tanks 6, 9, 13. One skilled in the art may also determine other appropriate system-addition points. The LAE and hops acids/organic acids can be added to a process vessel 6, 9, 13 such as a heatable conditioning tank 6, capable of performing liquefaction, or to a yeast propagation vessel 9. In variations, the process vessel 6, 9, 13 can also be a fermentation tank 13.

In an embodiment, the concentrations of bacteria and other undesirable microorganisms are reduced while propagation and/or conditioning of desirable microorganisms are encouraged. LAE 8 in combination with hops-acid extracts 7 and/or organic acids 7 is effective at reducing the concentration of bacteria and other undesirable microorganisms while simultaneously encouraging propagation and/or conditioning of desirable microorganisms 5. The combination of these products provides a synergistic, antimicrobial treatment without the use of man-made antibiotics.

In variations, the process is practiced by adding a small amount of hops-acid extract and/or organic acid; e.g., 0.5-120 ppm, 1-100 ppm, 2-70 ppm, 5-50 ppm, 5-45 ppm, 5-10 ppm [as measured in the system being treated]; in conjunction with LAE 8, results in a synergistic effect. In some non-limiting embodiments, hops acids 7 and/or organic acids 7 are added simultaneously with the LAE 8. In other embodiments, the hops acid 7 and/or organic acid 7 is added separately from the LAE 8 to the system being treated. The addition of hops-acid extracts 7 and/or organic acids 7 in conjunction with the addition of LAE 8 results in improved antimicrobial efficacy.

It should be appreciated by those of at least ordinary skill in the art that all references within this Section III to the production of fuel ethanol by yeast fermentation is intended to be merely an example, and is not intended to limit the scope of the application of the inventive disclosures contained herein. Other fermentation products which could employ the combination of LAE 8 and hops acids/organic acids 7 include distilled spirits, beer, wine, pharmaceuticals, pharmaceutical intermediates, baking products, nutraceuticals (foodstuff that provides health benefits, such as fortified foods and dietary supplements), nutraceutical intermediates, industrial chemical feedstocks, and enzymes. The methods/processes described herein can also be utilized to treat yeast used in the baking industry.

*Saccharomyces* yeasts are one type of useful yeast 5 such as *Saccharomyces cerevisiae*. Non-*Saccharomyces* yeasts can also be used in the invention. However, yeast 5 is not the only microorganism used in fermentation. Additional desirable fermenting microorganisms 5 could also be used and benefited by the invention such as the fungi and bacteria typically used in cellulosic ethanol production. Some examples of desirable fermenting microorganisms 5 include, but are not limited to, *Trichoderma reesei, Trichoderma viride, Clostridium ljungdahlii*, and genetically modified yeast.

Hops-acid extracts and organic acids 7 are useful for killing bacteria, while allowing yeast or other desirable producing microorganisms to survive and thrive. Fermentation industries typically apply hops-acid extracts 7 or organic acids 7 to propagation and fermentation solutions 3.

The LAE 8 and hops acid/organic acid 7 can be added at various points in the propagation, conditioning, and/or fermentation processes 3, 6, 9, 13. The LAE 8 and hops acid/organic acid 7 can be added to cook vessels, fermentation tanks 13, propagation tanks 6, conditioning tanks 9, starter tanks, or during liquefaction. The LAE 8 and hops acid/organic acid 7 can also be added directly to the corn mash 3. The LAE 8 and hops acid/organic acid 7 can also be added to the interstage-heat-exchange system or heat exchangers 14. The LAE 8 and hops acid/organic acid 7 can also be added to the piping between these units or heat exchangers 14.

The LAE 8 and hops acid/organic acid 7 can be added directly into the fermentation mixture 3. This can be done by adding the LAE 8 and hops acid/organic acid 7 in conjunction with the yeast 5 or other desirable microorganism 5 and fermentable carbohydrate 2; for example, during the simultaneous saccharification and fermentation (SSF) stage.

In a non-limiting embodiment, the hops-acid-extract 7 and/or organic acid 7 dosages of 0.5-120 ppm, 1-100 ppm, 2-70 ppm, 5-50 ppm, 5-45 ppm, 2-15 ppm, 3-10 ppm, or 5-10 ppm; and LAE 8 dosages of 100-2000 ppm, 200-1000 ppm, or ≥100 ppm can be added directly into the fermentation mixture 3.

The LAE 8 and hops acid/organic acid 7 can also be added to the mash 3 prior to the fermentation process. Hops-acid extract/organic acid 7 dosages of at 0.5-120 ppm, 1-100 ppm, 2-70 ppm, 5-50 ppm, 5-45 ppm, 2-15 ppm, 5-15 ppm, 5-10 ppm; and LAE 8 dosages of 100-2000 ppm or ≥100 ppm can be added to the mash 3 prior to fermentation.

LAE 8 and hops acid/organic acid 7 can also be added during propagation 6 and/or conditioning 9. For example, hops-acid extracts 7 and/or organic acids 7 can be added to the yeast 5 slurry, replacing an acid-washing step.

Cellulose-Based Ethanol Production

LAE 8, by itself, or in conjunction with hops acid/organic acid 7, can be also be used to achieve improved results in the production of cellulosic ethanol 15. Cellulosic ethanol 15 is a type of ethanol that is produced from cellulose, as opposed to the sugars and starches used in producing carbohydrate-based ethanol. Cellulose is present in non-traditional biomass sources such as switch grass, corn stover, and forestry. This type of ethanol production is particularly attractive because of the large availability of cellulose sources. Cellulosic ethanol, by the very nature of the raw material, introduces higher levels of contaminants and competing microorganisms into the fermentation process. Hops acid 7 and/or organic acid 7 used in conjunction with LAE 8 can be used in cellulosic-ethanol production to control undesirable microorganisms.

There are two primary processes of producing alcohol from cellulose. One process is a hydrolysis process that utilizes fungi; for example, *Trichoderma reesei* and/or *Trichoderma viride*. The other process is a gasification process using a bacteria such as *Clostridium ljungdahlii*. LAE 8, by itself, or in conjunction with hops acid 7 and/or organic acid 7, can be utilized in either process.

In the hydrolysis process, the cellulose chains are broken-down into five carbon and six carbon sugars before the fermentation process 13. This is either done chemically or enzymatically.

In the chemical hydrolysis method, the cellulose can be treated with dilute acid at high temperature and pressure or concentrated acid at lower temperature and atmospheric pressure. In the chemical hydrolysis process, the cellulose reacts with the acid and water to form individual sugar molecules. These sugar molecules are then neutralized and yeast fermentation is used to produce ethanol. LAE 8, by itself, or in conjunction with hops acid 7 and/or organic acid 7, can be used during the yeast fermentation portion of this method.

Enzymatic hydrolysis can be carried out using two methods: The first method is known as direct microbial conversion (DMC). The DMC method uses a single microorganism to convert the cellulosic biomass to ethanol 15. The ethanol 15 and required enzymes are produced by the same microorganism 5. LAE 8, by itself, or in conjunction with hops acid 7 and/or organic acid 7, can be used during the propagation 6, conditioning 9, and/or fermentation 13 steps with this specialized organism 5.

The second enzymatic hydrolysis method is known as the enzymatic hydrolysis method. In this method, cellulose chains are broken-down using cellulase enzymes 7. Cellulase enzymes 7 are typically present in the stomachs of ruminants, such as cows and sheep, in order to break-down the cellulose that they eat. The enzymatic method is typically carried out in four or five stages. The cellulose is pretreated to make the raw material, such as wood or straw, more amenable to hydrolysis. Next the cellulase enzymes 7 are used to break the cellulose molecules into fermentable sugars. Following hydrolysis, the sugars are separated from residual materials and added to the yeast 5. The hydrolyzate sugars are fermented to ethanol using yeast. Finally, the ethanol 15 is recovered by distillation 14. Alternatively, the hydrolysis and fermentation can be carried out together by using special bacteria or fungi that accomplish both processes. When both steps are carried out together, the process is called sequential hydrolysis and fermentation (SHF).

LAE 8, by itself, or in conjunction with hops acid 7 and/or organic acid 7, can be introduced for microbiological efficacy at various points in the enzymatic method of hydrolysis. LAE 8, by itself, or in conjunction with hops acid 7 and/or organic acid 7, can be used in the production, manufacture, and fermentation of cellulase enzymes made by *Trichoderma* and other fungi strains. LAE 8, by itself, or blended with hops acid 7 and/or organic acid 7, can be added in the cellulosic simultaneous saccharification and fermentation phase (SSF). LAE 8, by itself, or in conjunction with hops acid 7 and/or organic acid 7, can be introduced in the sequential hydrolysis and fermentation (SHF) phase. They could also be introduced at a point before, during, or after the fermentation by cellulolytic fungi that create the cellulase enzymes. Alternatively, LAE 8, by itself, or in conjunction with hops acid 7 and/or organic acid 7, can be added during the yeast fermentation phase, as discussed above.

The gasification process does not break the cellulose chain into sugar molecules. First, the carbon in the cellulose is converted to carbon monoxide, carbon dioxide, and hydrogen in a partial-combustion reaction. Then, the carbon monoxide, carbon dioxide, and hydrogen are fed into a special fermenter that uses a microorganism such as *Clostridium ljungdahlii* that is capable of consuming the carbon monoxide, carbon dioxide, and hydrogen to produce ethanol and water. Finally, the ethanol 15 is separated from the water 4 in a distillation step 14. LAE 8, by itself, or in conjunction with hops acid 7 and/or organic acid 7, can be used as an antimicrobial agent in the fermentation step 13 involving microorganisms 5 such as *Clostridium ljungdahlii* that are capable of consuming carbon monoxide, carbon dioxide, and hydrogen to produce ethanol 15 and water 4.

General Discussion of LAE-Additive Dosages

Laboratory testing, as discussed in Section II, supra, indicates that in most conditioning, propagation, and fermentation applications, LAE 8 appears to be most effective at concentrations from 5 ppm to 50 ppm, with 35 ppm being the preferred variation of the process. However, such preferred embodiments are not intended to be considered limiting of the inventive disclosures herein.

In one non-limiting embodiment, LAE 8, by itself, or in conjunction with hops acid and/or organic acid, is added to a tank 6, 9, 13 and diluted to a predetermined concentration at a predetermined ratio. In the tank 6, 9, 13, hops-acid extract, such as isomerized-alpha extract, and LAE are dissolved in water to form a LAE 8 and hops acid/organic acid blend. The concentration of the LAE solution 8, the hops-acid-extract solution, and the organic-acid solution in the batch tank 6, 9, 13 can vary across a wide range. The blended solution containing LAE 8 and containing hops-acid extract and/or organic acid solution is then exhausted from the batch tank through an outlet at a specified dosage to create a solution of the desired concentration.

In one non-limiting embodiment, the ratio of LAE 8 to acid 7 (whether hops acid and/or organic acid) is from a 1:200 to 1:10 ratio. The tank used is typically a pre-mix tank 3.

A process vessel 6, 9, 13 containing an aqueous microorganism solution 3 is fluidly connected to the batch tank via outlets on the batch tank. The process vessel 6, 9, 13 could be a cook vessel, fermentation tank 13, conditioning tank 6, starter tank 3, propagation tank 9, liquefaction vessel 19, and/or piping or heat exchanger 21 between these units. The solution 3 containing LAE and acid (hops acid and/or organic acid) in the process vessel 6, 9, 13 is capable of promoting propagation of producing microorganism present while simultaneously decreasing the concentration of undesirable microorganisms.

The LAE 8, by itself, or in conjunction with hops acid 7 and/or organic acid 7, can be combined and then added to the system to be treated. They may also be added sequentially or separately to the system to be treated. The ratio of acids 7 (whether hops acid and/or organic acid) to LAE 8 that are added to the systems to be treated can be as high as from 1:6000 to 1:5, or 1:6000 to 1:10, or 1:500 to 1:10, or 1:200 to 1:20, or 1:100 to 1:10, or 1:100 to 1:20.

The LAE can be used in amounts of from 12500 ppm down to 0.5 ppm in the invention, from 6250 down to 0.5 ppm, or from 4000 down to 0.5 ppm, or from 4000 down to 2 ppm, or from 1000 down to 0.5 ppm, or from 1000 down to 200 ppm. Generally, at least 0.5 ppm or at least 200 ppm or at least 300 ppm of LAE is used. Hops acid could be used in amount of at least 0.5 ppm and less than 120 ppm or between 1 ppm and 100 ppm, or between 2 and 70 ppm or between 5 and 50 ppm or between 5 and 45 or 0.5 ppm to 20 ppm, or from 0.5 ppm to 15 ppm, or from 2 to 15 ppm, or from 2 to 12 ppm, or from 3 to 12 ppm, or from 3 to 10 ppm. Generally, the amount of hops acid used in the invention is at least 2 ppm or at least 3 ppm. LAE compounds 8 that can be used in the invention LAEPro™ and LAEPro™ S50. The main components of the present inventive disclosure (LAE 8 and acid 7 [hops acid and/or organic acid]) can be added to the aqueous system 3 separately or blended prior to addition. The LAE compounds 8 can be added to the aqueous side systems with other additives 7 such as, but not necessarily restricted to, surfactants, scale and corrosion control compounds, ionic or non-ionic polymers, pH control agents, and other additives used for altering or modifying the chemistry of the aqueous system 3.

A person of ordinary skill in the art using the teachings described herein can determine the concentration of the composition required to achieve acceptable microbial control, and that the concentration is dependent on the matrix.

When used in a fermentation system, the LAE/hops acid/organic acid blend 8, 7 can be added in various locations in the fermentation system such as can be added in single or multiple locations in the fermentation process, including the slurry tank(s), cookers, mash coolers, propagators, and fermentation tanks 3, 6, 9, 13. One skilled in the art may also determine other addition points.

IV. A Preservative and Method for Optimizing the Shelf Life of High-Moisture Organic Materials The inventive disclosures presented in this Section IV are directed generally to a preservative comprised of Lauryl-L-arginine ethyl ester monohydrochloride (aka "Lauric arginate" or "LAE") for high-moisture organic material (such as grain products having a high water activity or moisture content). In some embodiments, said high-moisture organic material includes byproduct distiller's grains produced as a result of the inventive disclosures discussed in Sections II and III, supra, and depicted in FIGS. 3A-3B, which in some variations is also blended with one or more organic acids.

In one embodiment, the organic acids are selected from the group consisting of propionic acid, benzoic acid, citric acid, phosphoric acid, and sorbic acid. Preservatives based only on LAE 8 and preservatives based on LAE 8 combined with organic acid(s) 7 are efficacious.

LAE 8 and organic acids 7 are widely used as preservatives in the food industry. LAE 8 and each organic acid 7 has a distinct spectrum of activity against microorganisms, specifically molds, yeasts, and aerobic bacteria, that contribute to spoilage in feeds. (See, e.g., Higgins, C. and Brinkhaus, F. "Efficacy of several organic acids against molds." 1999. J. Applied Poultry Res. 8:480-487.) Accordingly, it is usually desirable to use a blend of organic acids 7 with a preservative such as LAE 8 to achieve a spectrum of efficacy of each of the components will complement each other to provide efficacy over a broad range of microorganisms. These efficacies should be taken into account in optimizing the LAE 8 and organic acids 7 selected for use when practicing the inventive disclosures herein.

The rate of LAE-based preservative 8 application is dependent on the material being treated. In an embodiment, the LAE-based preservative 8 is applied at a rate of between about 2 lbs. and about 50 lbs. per ton of distiller's grain 28, 30, and the organic acid(s) 7 is included at a rate of between approximately 0.0005% and approximately 0.70% by weight.

Embodiments of the preservative disclosures herein greatly extend the time over which such materials may be stored prior to spoilage. The present preservative composition is particularly suited for application to byproducts of grain processing. Materials having characteristics that make them suitable for preservation by the present inventive disclosures include organic materials that have a water activity ($A_w$) that supports the growth of molds, yeasts, and/or gram-positive/gram-negative bacteria. While some microbes, such as *Clostridium botulinum*, stop growing at a water activity $A_w$<0.95, yeasts and molds will continue to grow at a water activity $A_w$ of as little as 0.7 to 0.75. Most pathogenic aerobic bacteria stop growing at a water activity $A_w$ of around 0.90. Commercial grain products having these characteristics include wet-corn gluten feed, wet/dry distiller's grains, fuzzy cottonseed, wet and dry brewer's grains, cottonseed meal, corn hominy feed, almond hulls, wet and dry sugar beet pulp, canola meal, citrus pulp, rice bran, safflower meal, soybean hulls, food-processing waste, and wheat-mill run. Of course, a great many other products have such characteristics, including many food products.

In some embodiments, the process of applying the LAE preservative to distiller's grain also includes a mixture of organic acids such as citric acid, propionic acid, benzoic acid, and/or sorbic acid. Those skilled in the art would also appreciate that modifications of the materials, combinations of materials, and rates of inclusion may be made to obtain the desired results.

In other embodiments, the LAE-based preservative composition 8 is applied to wet distiller's grains 28, 30 in a manner that incorporates the teachings of an Aug. 6, 2004 Final Report to Kremin Americas, Inc. concerning the "Efficacy of a Preservative Product (ZeniPro) for Wet Distiller's Grains", but instead substituting the LAE-based preservatives 8 disclosed herein for the ZeniPro™ product that is specified in Appendix D of U.S. Patent Application No. 62/197,994, which is incorporated by reference.

In an embodiment, a blend of LAE 8 and citric acid 7 is used as the preservative agent; however, this particular blend of is not necessary to the practice of the inventive disclosures contemplated herein.

V. A Method for Controlling Undesirable Microorganism Concentration in an Aqueous Fluid Solution Employed in a Fermentation Process The inventive disclosures presented in this Section V are directed generally to a process and associated systems for improving yeast conditioning and propagation, leading to improved fermentation processes and yields. In one embodiment, solutions containing yeast are introduced to an effective amount of Lauryl-L-arginine ethyl ester monohydrochloride (aka "Lauric arginate" or "LAE") based on the teachings of Sections II through IV, supra, to inhibit the population of competing bacteria and other undesired microorganisms without having to use antibiotics. In variations, the yeast solution is also exposed to an effective amount of hops acid and/or organic acid in conjunction with the LAE.

Figure 3B:
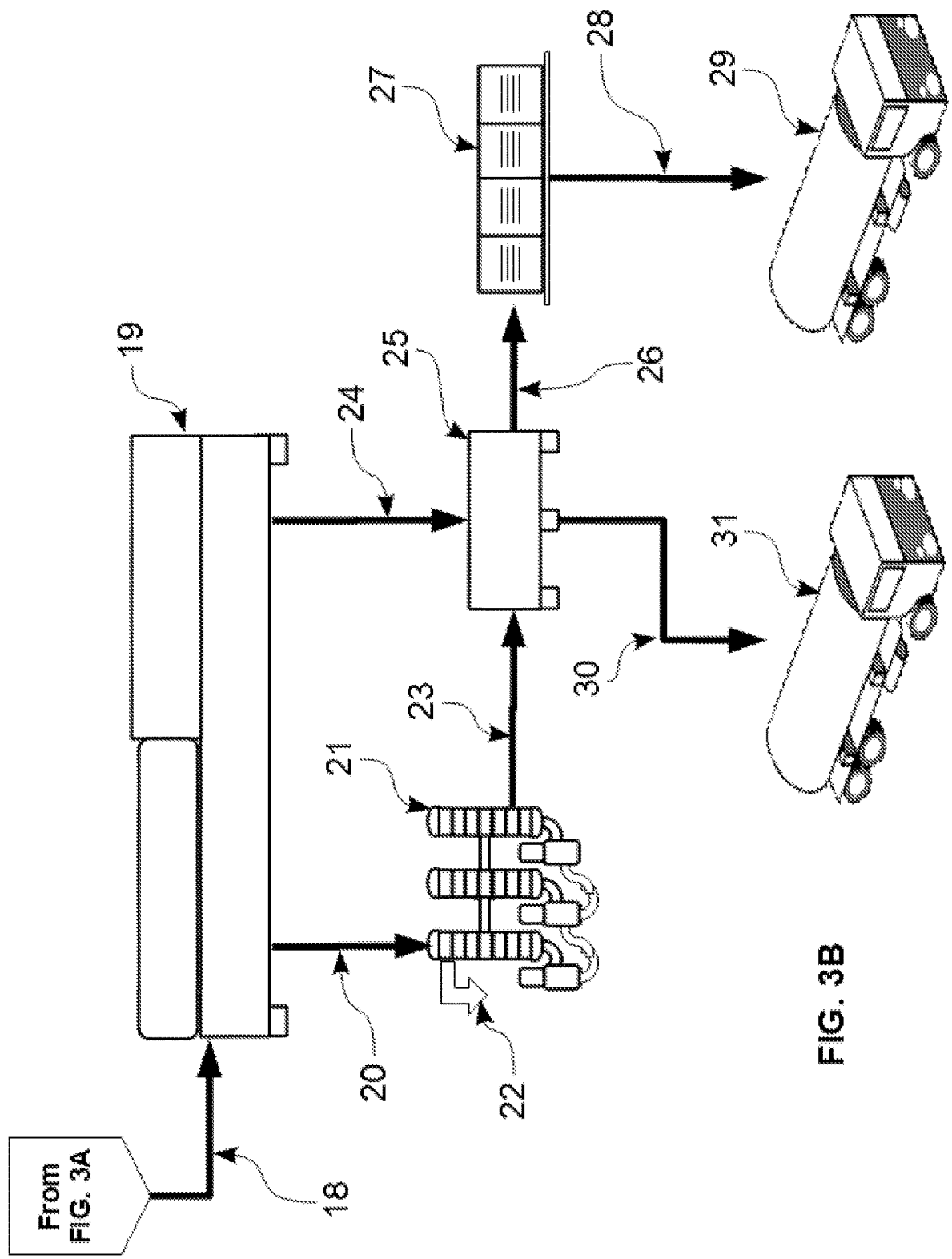
FIG. 3B depicts one embodiment of the processing and storage of distiller's grains and solubles that are byproducts (i.e., whole stillage) from the propagation, conditioning, and fermentation process for the distillation-process production of alcohol-based products (e.g., ethanol, beverage alcohol, etc.) depicted in FIG. 3A.

Refer to FIGS. 3A-3B. The method comprises the steps of:
  Introducing a fermentable carbohydrate 2 to the aqueous solution 3;
  Introducing at least one desirable microorganism 5 that is capable of fermenting carbohydrate to the aqueous fluid solution 3; and
  Introducing at least one LAE compound 8 into the aqueous fluid solution 3.

In some embodiments, the performance of the above method steps are not necessarily performed in the order presented.

In variations, the method can be enhanced by further comprising the step of introducing at least one acid 7 into the aqueous fluid solution 3, wherein the at least one acid 7 is selected from the group consisting of hops acid, organic acid, or a combination of hops acid and organic acid.

In other variations, the LAE compound 8 is selected from the group consisting of LAEPro™, LAEPro™ S50, MIRENAT®-P/100, and MIRENAT®-GA.

In still more variations, the at least one desirable microorganism 5 is selected from the group consisting of a yeast, a fungi, a bacteria, and combination thereof.

In some embodiments, the concentration of the at least one acid 7 in said aqueous fluid solution 3 is in the range of 1 ppm to 100 ppm. In variations, the concentration of the at least one acid 7 in the aqueous fluid solution 3 is in the range of 2 ppm to 70 ppm. In even more variations, the dosage of the at least one acid 7 is at least 0.5 ppm.

In many embodiments, the LAE compound 8 has a dosage of at least 0.5 ppm and less than or equal to 35 ppm. In additional embodiments, the LAE compound 8 is LAEPro™ LAEPro™ S50, MIRENAT®-P/100, or MIRENAT®-GA, and the ratio of the at least one acid 7 to LAE compound 8 is from 1:10 to 1:6500.

VI. A Method for Reducing Residual By-Product of Antibiotic Substances in a Fermentation Process The inventive disclosures presented in this Section VI are directed generally to a process and associated systems for improving yeast conditioning and propagation, leading to improved fermentation processes and yields, while also reducing or removing residual byproduct antibiotic substances from the end products. In one embodiment, solutions containing yeast are introduced to an effective amount of Lauryl-L-arginine ethyl ester monohydrochloride (aka "Lauric arginate" or "LAE") based on the teachings of Sections II through V, supra, to inhibit the population of competing bacteria and other undesired microorganisms without having to use antibiotics. In variations, the yeast solution is also exposed to an effective amount of hops acid and/or organic acid in conjunction with the LAE.

Refer to FIGS. 3A-3B. The method comprises the steps of:
  Introducing a fermentable carbohydrate 2 to the aqueous solution 3;
  Introducing at least one desirable microorganism 5 to said aqueous fluid solution 3; and
  Introducing at least one LAE compound 8 into the aqueous fluid solution 3.

In some embodiments, the performance of the above method steps are not necessarily performed in the order presented.

In variations, the method can be enhanced by further comprising the step of introducing at least one acid 7 into the aqueous fluid solution 3, wherein the at least one acid 7 is selected from the group consisting of hops acid, organic acid, or a combination of hops acid and organic acid.

In other variations, the LAE compound 8 is selected from the group consisting of LAEPro™, LAEPro™ S50, MIRENAT®-P/100, and MIRENAT®-GA.

In still more variations, the at least one desirable microorganism 5 is selected from the group consisting of a yeast, a fungi, a bacteria, and combination thereof.

In some embodiments, the concentration of the at least one acid 7 in said aqueous fluid solution 3 is in the range of 1 ppm to 100 ppm. In variations, the concentration of the at least one acid 7 in the aqueous fluid solution 3 is in the range of 2 ppm to 70 ppm. In even more variations, the dosage of the at least one acid 7 is at least 0.5 ppm.

In many embodiments, the LAE compound 8 has a dosage of at least 0.5 ppm and less than or equal to 35 ppm. In additional embodiments, the LAE compound 8 is LAEPro™

LAEPro™ S50, MIRENAT®-P/100, or MIRENAT®-GA, and the ratio of the at least one acid 7 to LAE compound 8 is from 1:10 to 1:6500.

VII. A System for Controlling Undesirable Microorganism Concentration in an Aqueous Fluid Solution Employed in a Fermentation Process The inventive disclosures presented in this Section VII are directed generally to system for improving yeast conditioning and propagation, leading to improved fermentation processes and yields. In one embodiment, the system's solutions containing yeast are introduced to an effective amount of Lauryl-L-arginine ethyl ester monohydrochloride (aka "Lauric arginate" or "LAE") based on the teachings of Sections II through VI, supra, to inhibit the population of competing bacteria and other undesired microorganisms without having to use antibiotics. In variations, the yeast solution is also exposed to an effective amount of hops acid and/or organic acid in conjunction with the LAE.

Refer to FIGS. 3A-3B and Sections II and III. The system comprises:
- A means for introducing a fermentable carbohydrate 2 to the aqueous solution 3;
- A means for introducing at least one desirable microorganism 5 that is capable of fermenting carbohydrate to the aqueous fluid solution 3; and
- A means for introducing at least one LAE compound 8 into the aqueous fluid solution 3.

In variations, the method can be enhanced by further comprising a means for introducing at least one acid 7 into the aqueous fluid solution 3, wherein the at least one acid 7 is selected from the group consisting of hops acid, organic acid, or a combination of hops acid and organic acid.

In other variations, the LAE compound 8 is selected from the group consisting of LAEPro™, LAEPro™ S50, MIRENAT®-P/100, and MIRENAT®-GA.

In still more variations, the at least one desirable microorganism 5 is selected from the group consisting of a yeast, a fungi, a bacteria, and combination thereof.

In some embodiments, the concentration of the at least one acid 7 in said aqueous fluid solution 3 is in the range of 1 ppm to 100 ppm. In variations, the concentration of the at least one acid 7 in the aqueous fluid solution 3 is in the range of 2 ppm to 70 ppm. In even more variations, the dosage of the at least one acid 7 is at least 0.5 ppm.

In many embodiments, the LAE compound 8 has a dosage of at least 0.5 ppm and less than or equal to 75 ppm. In additional embodiments, the LAE compound 8 is LAEPro™ LAEPro™ S50, MIRENAT®-P/100, or MIRENAT®-GA, and the ratio of the at least one acid 7 to LAE compound 8 is from 1:10 to 1:6500.

VIII. A Composition for Preserving Distiller's Grains, Associated Grain Products, and/or Other Plant Biomass The inventive disclosures presented in this Section VIII are directed generally to a composition for preservative comprised of Lauryl-L-arginine ethyl ester monohydrochloride (aka "Lauric arginate" or "LAE") for high-moisture organic material (such as grain products having a high water activity or moisture content). In some embodiments, the high-moisture organic material includes byproduct distiller's grains produced as a result of the inventive disclosures discussed in Sections II through VII, supra, and depicted in FIGS. 3A-3B, which in some variations is also blended with one or more organic acids.

In an embodiment, the composition for preserving distiller's grains, associated grain products, and/or other plant biomass is intended for distiller's grains, associated grain products, and/or other plant biomass having a total moisture content of >11% and water activity greater than 0.10 and less than 0.90, with initial levels of microbes that cause spoilage of the grain product. Moreover, the composition 8 comprises:
- 10% to 99.9% by weight of LAE,
    - Wherein the composition 8 is applied to said distiller's grains, associated grain products, and/or other plant biomass at a concentration of 0.05% to 30.0% by weight in order to maintain or reduce the level of microbes in the grain product at or below the initial levels for a period of not less than seven days.

In variations, the composition 8 further comprises one or more organic acids 7 selected from the group consisting of propionic acid, sorbic acid, citric acid, ascorbic acid, benzoic acid, and phosphoric acid. In some variations, the concentration of the one or more organic acids 7 is of 5% to 70% by weight.

In some embodiments, the LAE compound 8 of the composition 8 is selected from the group consisting of LAEPro™, LAEPro™ S50, MIRENAT®-P/100, and MIRENAT®-GA.

IX. A Method of Using a Composition for Preserving Distiller's Grains, Associated Grain Products, and/or Other Plant Biomass The inventive disclosures presented in this Section IX are directed generally to a method of using a composition for preservative comprised of Lauryl-L-arginine ethyl ester monohydrochloride (aka "Lauric arginate" or "LAE") for high-moisture organic material (such as grain products having a high water activity or moisture content). In some embodiments, the high-moisture organic material includes byproduct distiller's grains produced as a result of the inventive disclosures discussed in Sections II through VIII, supra, and depicted in FIGS. 3A-3B, which in some variations is also blended with one or more organic acids.

In an embodiment, the method of using a composition 8 for preserving distiller's grains, associated grain products, and/or other plant biomass is intended for distiller's grains, associated grain products, and/or other plant biomass having a total moisture content of >10% and water activity greater than 0.10 and less than 0.90, with initial levels of microbes that cause spoilage of the grain product. Moreover, the method comprises the steps of:
- Obtaining a composition 8 for preserving distiller's grains and/or associated grain products, said distiller's grains and associated grain products having a water activity greater than 0.10 and less than 0.90, with initial levels of microbes that cause spoilage of the grain product, according to Section VIII, supra; and
- Adding an effective amount of said preservative composition to a distiller's grain, an associated grain products, and/or other plant biomass.

In variations, the distiller's grain, associated grain product, and/or other plant biomass to be preserved is selected from the group consisting of wet-corn gluten feed, wet distiller's grains with or without solubles, distiller's dried grains, fuzzy cottonseed, wet and dry brewer's grains, cottonseed meal, corn hominy feed, almond hulls, wet and dry sugar beet pulp, canola meal, citrus pulp, rice bran, safflower meal, soybean hulls, food processing waste, wheat-mill run, switch grass, corn stover, and forestry plants.

In other variations, the distiller's grain, associated grain product, and/or other plant biomass to be preserved is a *cannabis*-related biomass in jurisdictions where such operations are legally allowed.

In some embodiments, the effective amount of the preservative composition is in the range of 0.05 ppm to 75.0 ppm of LAE-based preservative.

In even more embodiments, the effective amount of said preservative composition 8 is applied at a rate of greater than or equal to 2 lbs. and less than or equal to 50 lbs. per ton of distiller's grains, associated grain products, and/or other plant biomass. In variations, the preservative composition incorporates organic acid(s) included at a rate of between greater than or equal to 0.0005% and less than or equal to 0.70% by weight.

X. An Ethanol Product-by-Process (and Associated by-Products) that is Substantially Free of Undesirable Microorganisms and Man-Made Antibiotics The inventive disclosures presented in this Section X are directed generally to an ethanol product-by-process that is substantially free of undesirable microorganisms as well as manmade antibiotics, produced as a result of the inventive disclosures discussed in Sections II though IX, supra, and depicted in FIGS. 3A-3B. The process/method by which the product-by-process is produced comprises the steps of:
  Introducing a fermentable carbohydrate 2 to the aqueous fluid solution 3;
  Introducing at least one desirable microorganism 5 to the solution; and
  Introducing at least one LAE compound into the solution.
In variations, the at least one desirable microorganism 5 is selected from the group consisting of a yeast, a fungi, a bacteria, and combination thereof.

In some embodiments, the at least one LAE compound 8 is selected from the group consisting of LAEPro™, LAE-Pro™ S50, MIRENAT®-P/100, and MIRENAT®-GA.

In more embodiments, the process to produce the ethanol product further comprises the step of introducing at least one acid 7 into the solution, wherein the at least one acid 7 is selected from the group consisting of hops acid, organic acid, or a combination of hops acid and organic acid. In variations, the concentration of the at least one acid 7 in the aqueous fluid solution 3 is in the range of 1 ppm to 100 ppm. In alternative variations, the concentration of the at least one acid 7 in the aqueous fluid solution 3 is in the range of 2 ppm to 70 ppm. In still more variations, the dosage of the at least one acid is at least 0.5 ppm.

In some embodiments, the LAE compound 8 has a dosage of at least 0.05 ppm and less than or equal to 75.0 ppm.

In additional embodiments, byproducts 18 from the fermentation and distillation processes are separated from the ethanol 14 by performing the steps of:
  Separating ethanol 14 from whole stillage byproducts 18; and
  Storing said separated ethanol;
  Whereby the ethanol 14 is substantially free of man-made antibiotics.
In even more embodiments, byproducts 18 from the fermentation and distillation processes are further processed by performing the step of separating said whole-stillage byproducts 18 into solid particulates 24 and thin stillage 20.

In variations, the thin stillage 20 is further processed by performing the steps of:
  Subjecting said thin stillage 20 to evaporation processes 21 to release condensed vapors 22; and
  Transferring the evaporation-processed thin-stillage 23 byproduct to storage 25.

In some variations, the solid particulates 24 are subjected to the step of simply being transferred to storage 25, whereby the storage 25 contains distiller's grains and solubles 30 that are substantially man-made antibiotic-free. In some cases, an effective amount of additional LAE compound 8 is added to the storage 25, 31 to enhance the preservation of the stored byproducts 30.

In further variations, the distiller's grains and solubles 30 is further processed by performing the steps of:
  Subjecting separated solid particulates 26 to a drying process to create distiller's grains and solubles 28; and
  Transferring said distiller's dried grains and solubles 28 to storage 29;
  Whereby the storage 29 contains distiller's grains and solubles that are substantially man-made antibiotic-free.
In some cases, an effective amount of additional LAE compound 8 is added to the storage 29 to enhance the preservation of the stored byproducts 28.

XI. Alternative Embodiments and Other Variations

The various embodiments and variations thereof described herein, including the descriptions in any appended Claims and/or illustrated in the accompanying Figures, are merely exemplary and are not meant to limit the scope of the inventive disclosure. It should be appreciated that numerous variations of the inventive disclosures herein have been contemplated as would be obvious to one of ordinary skill in the art with the benefit of this disclosure.

Hence, those ordinarily skilled in the art will have no difficulty devising myriad obvious variations and improvements to the invention, all of which are intended to be encompassed within the scope of the Description, Claims, and Figures herein.

The invention claimed is:

1. A method of controlling undesirable gram-positive microorganism concentration in a fermentation mixture and in a plant biomass, the method comprising the steps of:
  introducing a fermentable carbohydrate to the fermentation mixture;
  introducing at least one desirable microorganism that is capable of fermenting the fermentable carbohydrate to the fermentation mixture; and
  introducing a first at least one Ethyl Lauroyl Arginate compound to the fermentation mixture;
  distilling the fermentation mixture to produce whole stillage byproducts;
  separating the plant biomass from the whole stillage byproducts, wherein the plant biomass has a total moisture content as low as about 11%; and
  applying a second at least one Ethyl Lauroyl Arginate compound to the plant biomass.

2. The method of claim 1, wherein said at least one desirable microorganism is selected from the group consisting of a yeast, a fungi, a bacteria, and combination thereof.

3. The method of claim 1, wherein the steps are performed sequentially in the order provided in claim 1.

4. The method of claim 1, wherein the concentration of the first at least one Ethyl Lauroyl Arginate compound in the fermentation mixture is in the range of 1 ppm to 100 ppm.

5. The method of claim 1, wherein the first at least one Ethyl Lauroyl Arginate compound has a dosage of at least 0.5 ppm and less than or equal to 75 ppm.

6. The method of claim 1, further comprising including organic acid in the fermentation mixture at a concentration of between about 0.0005% and about 0.70% by weight.

7. The method of claim 1, further comprising increasing shelf life of the plant biomass.

8. A method of controlling undesirable microorganism concentration in a fermentation mixture and in a plant biomass, the method comprising the steps of:
- introducing a fermentable carbohydrate to the fermentation mixture;
- introducing at least one desirable microorganism that is capable of fermenting the fermentable carbohydrate to the fermentation mixture;
- introducing a first at least one Ethyl Lauroyl Arginate compound to the fermentation mixture;
- distilling the fermentation mixture to produce whole stillage byproducts;
- separating the plant biomass from the whole stillage byproducts, wherein the plant biomass has a total moisture content as low as about 11%; and
- applying a second at least one Ethyl Lauroyl Arginate compound to the plant biomass.

9. The method of claim 8, further comprising adding an effective amount of the second at least one Ethyl Lauroyl Arginate compound to enhance preservation of the plant biomass for up to seven days.

10. The method of claim 8, wherein the plant biomass is substantially free of man-made antibiotics.

11. The method of claim 8, wherein the plant biomass is wet distiller's grain.

12. The method of claim 8, wherein the undesirable microorganism is gram-positive bacteria.

13. The method of claim 8, wherein the fermentation mixture is at about 31° C.

14. The method of claim 1, wherein the fermentable carbohydrate is sourced from corn, cereal grains, cellulose-starch bearing materials, sugar cane, beets, or agave.

15. The method of claim 1, wherein the plant biomass is substantially free of man-made antibiotics.

16. The method of claim 1, wherein the plant biomass is wet distiller's grain.

17. The method of claim 1, wherein the fermentation mixture is at about 31° C.

18. The method of claim 1, further comprising adding an effective amount of the second at least one Ethyl Lauroyl Arginate compound to enhance preservation of the plant biomass for up to seven days.

* * * * *